(12) United States Patent
Wu

(10) Patent No.: US 6,897,408 B2
(45) Date of Patent: May 24, 2005

(54) ELECTRICALLY CONDUCTIVE AND HEATING WIRE CONTAINING FABRIC

(75) Inventor: Ming-Lai Wu, Taipei (TW)

(73) Assignee: Tai Lai Sporting Goods Enterprises Co., Ltd., Taipei (TW)

(*) Notice: Subject to any disclaimer, the term of this patent is extended or adjusted under 35 U.S.C. 154(b) by 0 days.

(21) Appl. No.: 10/329,343

(22) Filed: Dec. 27, 2002

(65) Prior Publication Data

US 2004/0124187 A1 Jul. 1, 2004

(51) Int. Cl.[7] ............................................. H05B 1/00
(52) U.S. Cl. ..................... 219/211; 219/212; 219/528; 219/529; 219/544; 219/549; 392/432
(58) Field of Search ............................... 219/211, 212, 219/213, 217, 528, 529, 544, 545, 549; 392/425, 432, 435

(56) References Cited

U.S. PATENT DOCUMENTS

| | | | | |
|---|---|---|---|---|
| 5,148,002 A | * | 9/1992 | Kuo et al. .................. | 219/211 |
| 5,986,243 A | * | 11/1999 | Campf ........................ | 219/529 |
| 6,172,344 B1 | * | 1/2001 | Gordon et al. ............... | 219/529 |
| 6,211,493 B1 | * | 4/2001 | Bouman ...................... | 219/213 |
| 6,255,799 B1 | * | 7/2001 | Le et al. ...................... | 219/211 |

\* cited by examiner

*Primary Examiner*—Fadi H. Dahbour
(74) *Attorney, Agent, or Firm*—Bacon & Thomas PLLC

(57) ABSTRACT

The present invention is related to an electrically conductive and heating wire containing fabric. The fabric is made of metal yarn and natural fiber. After a yarn covering process (covering metal yarn with short staple yarn), a circular loom is used to weave circular hollow heating wire containing fabric in the desired dimensions (0.1 cm~5 cm). After that, the heating wire containing fabric is pressed into flat shape. Then, the fabric is covered with natural long fiber or short staple, such as wool and rabbit fur. The wire containing fabric will be made into different types of products according to user demand (like rehabilitation equipment or insulating clothes). Thus, convenience is provided for use of the product and wide range of applications can be found for the present invention.

7 Claims, 5 Drawing Sheets

ELECTRICALLY CONDUCTIVE AND HEATING WIRE CONTAINING FABRIC

FIELD OF THE INVENTION

The present invention is related to the manufacturing technology and applications for the finished product of a wire containing fabric, especially an electrically conductive and heating wire with broad application range.

BACKGROUND OF THE INVENTION

In general, the conductive heating wire containing fabric used in rehabilitation equipment is made of metallic material through a bundle of multiple iron wires or multiple carbon fibers or a coil of a single iron wire or carbon fiber that is covered up by fabric. When it is in use, electric current (AC or DC) passes the heating wire to generate heat and provide thermal therapy to the patient who has the injured area covered by the fabric.

Because the above-mentioned traditional heating wire mostly uses alternative current (AC) as power source, it also produces hazardous electromagnetic wave and brings about serious safety concerns. Usually, the heating wire lacks the capability to reach a sufficiently high temperature (the maximum temperature is merely 35~45° C.). Its heating rate is slow and its heating intensity is not strong enough. It can not provide a satisfactory thermal therapy effect. Besides, in practical use it takes about four minutes for the heating wire to reach the maximum temperature. The heating rate is too slow to assure its performance in cold climate area. Even if the heating wire uses direct current (DC) as the power source, the continuous electric discharge will quickly deplete battery power and fails to provide desirable thermal therapy effect.

Apparently, the traditional heating wire gives the maximum temperature around 35° C., the adjustable temperature range is not wide enough to provide practical value in use. Further, when the power source is AC, space limitation appears to cause many inconveniences. Furthermore, the continuous electric discharge costs significant power consumption. Furthermore, the temperature setting is both non-adjustable and non-displayable, there is no way to know whether the set temperature is reached.

Therefore, the traditional heating wire needs further improvement.

The inventor for the present invention found the traditional heating wire could not function satisfactorily, so it further deteriorate the performance of the product that contains the heating wire. To assure the effect obtained from using therapy or rehabilitation equipment by the general public, the inventor for the present invention invented an innovative "electrically conductive and heating wire containing fabric" through many experiments and improvements on different raw materials and manufacturing processes.

SUMMARY OF THE INVENTION

The main objective for the present invention, "electrically conductive and heating wire containing fabric", is to provide a manufacturing process and applications (such as rehabilitation and insulating clothes) for a useful heating wire containing fabric. The wire containing fabric made from such a process possesses both electric conductivity and heating capability, so it can achieve the desirable performance for various applications. The application range and benefits for using the said wire-containing fabric are thus improved.

To reach the above objective, the present invention for "electrically conductive and heating wire containing fabric" adopts metal yarn and natural fiber in different metal wire or carbon fiber than before in a manufacturing process. Then, it is fabricated into a circular hollow rod, followed by flattening into stripe. Finally, it is covered by natural long (short) fiber. When the wire containing fabric is used for auxiliary rehabilitation equipment, a piece of the fabric is laid inside rubber foam substrate with one end extending out to a temperature controller that has a lithium battery and a control chip. During the use, medicine is applied to the injured area, which is then covered by the rehabilitation equipment. The temperature controller helps to keep the wire containing fabric heating up continuously at a constant temperature. Thus, blood circulation and metabolism will be promoted to provide rehabilitation effect. Further, the rehabilitation equipment can be operated by a wireless remote control, so it forms a combination of a subunit (auxiliary rehabilitation equipment) and a main unit (a remote control). Thus, the user can obtain the convenience for using the equipment from using such a remote control mode. This design can further extend the application to a main unit (a remote control) with unlimited number of subunits (rehabilitation equipment). It only needs to add several buttons for the subunits to the remote control. For operation, each subunit is set with temperature and time. Then the main units cover up different injured areas for a single user or multiple users. In this way, within a certain range of effectiveness it provides simple and convenient operation and rehabilitation effect to a single user or multiple users.

When such a heating wire containing fabric is used in cold area for insulation, it adopts the above-mentioned structural design in rehabilitation equipment. Around the substrate, there will be several joint structures like female-male fasteners or Velcro to match the similar joint structures on clothes, so the unit can be integrated with the clothes. When the user wears the clothes, insulation is provided through direct control or remote control to obtain the optimum temperature setting.

To further explain the objectives, characteristics and advantages for the present invention "conductive and heating wire containing fabric" to the examiners, the following will give a detailed description for the entire manufacturing process.

DETAILED DESCRIPTION OF THE INVENTION

The present invention is to provide an electric conductive and heating wire containing fabric. Its content covers the manufacturing process and the finished products for the wire containing fabric.

Figure 1:
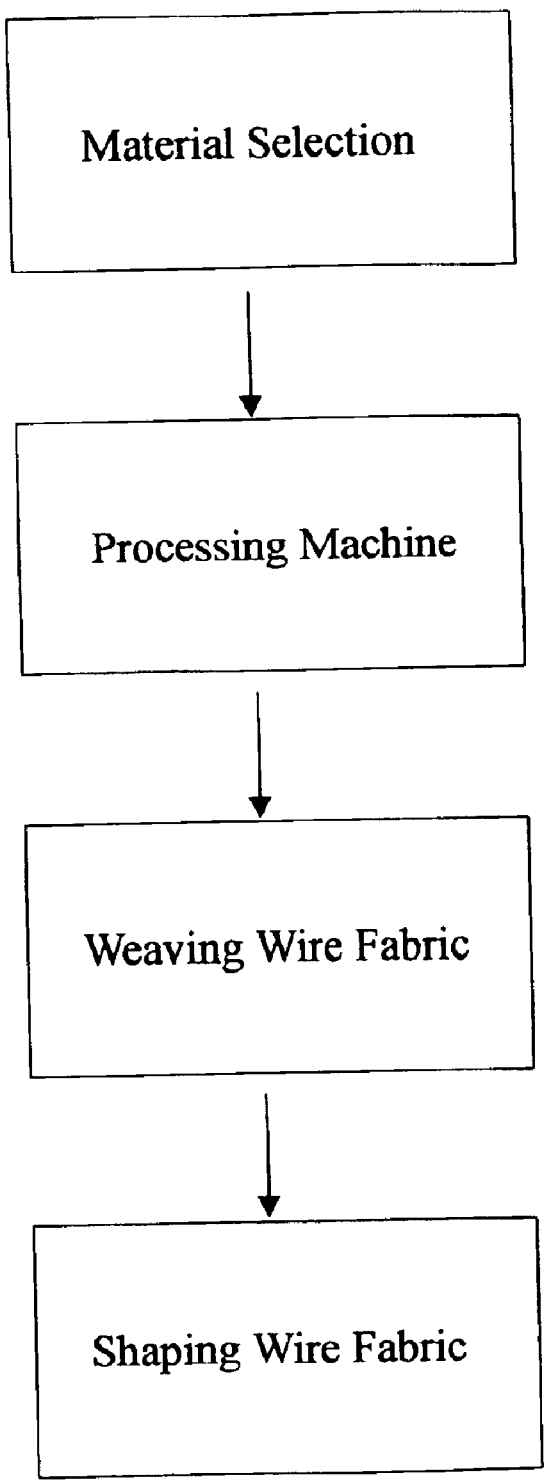
FIG. 1 is a manufacturing process for the wire containing fabric for the present invention.

1. The manufacturing process will include the procedures below: Please refer to FIG. 1 for the raw material selection, which will be based on the following things.

(1) preferably, metal yarn with good conductivity and diameter between 0.035~0.08 mm;

(2) natural (short) staple, like wool, rabbit fur, or far-IR treated silk, or elastic silk In the aspect of processing equipment:

Through yarn feeding equipment, the above-mentioned metal yarn and natural fiber are subject yarn covering operation, so the natural fiber is covered externally by metal yarn to reach an optimum coverage density (without broken wire as prerequisite). It is preferable to form a 1-cm natural fiber wrapped by 3~64 coils of metal yarn. Thus, the flatness for the wrapped metal wire is consistent to assure a stable therapy effect at a low frequency.

In the aspect of weaving the wire fabric:

The above coiled metal wire is sent to a circular loom in a weaving process to be fabricated into a circular hollow wire fabric within certain range of dimension (0.1~5 cm) (if for other applications, it can also be fabricated into any shape to meet the practical requirements).

In the aspect of shaping wire fabric:

The above circular hollow wire fabric is pressed into flat shape to maintain consistent conductivity. Finally, its surface is covered by natural long fiber or short staple like wool or rabbit fur to provide a comfortable feeling.

Through the above procedures, the "electrical conductive and heating wire containing fabric" for the present invention can be produced.

2. Product Applications

According to user requirements, the above shaped wire fabric is manufactured into various finished products, like low frequency therapy, thermal rehabilitation or insulation in cold area.

Figure 2:
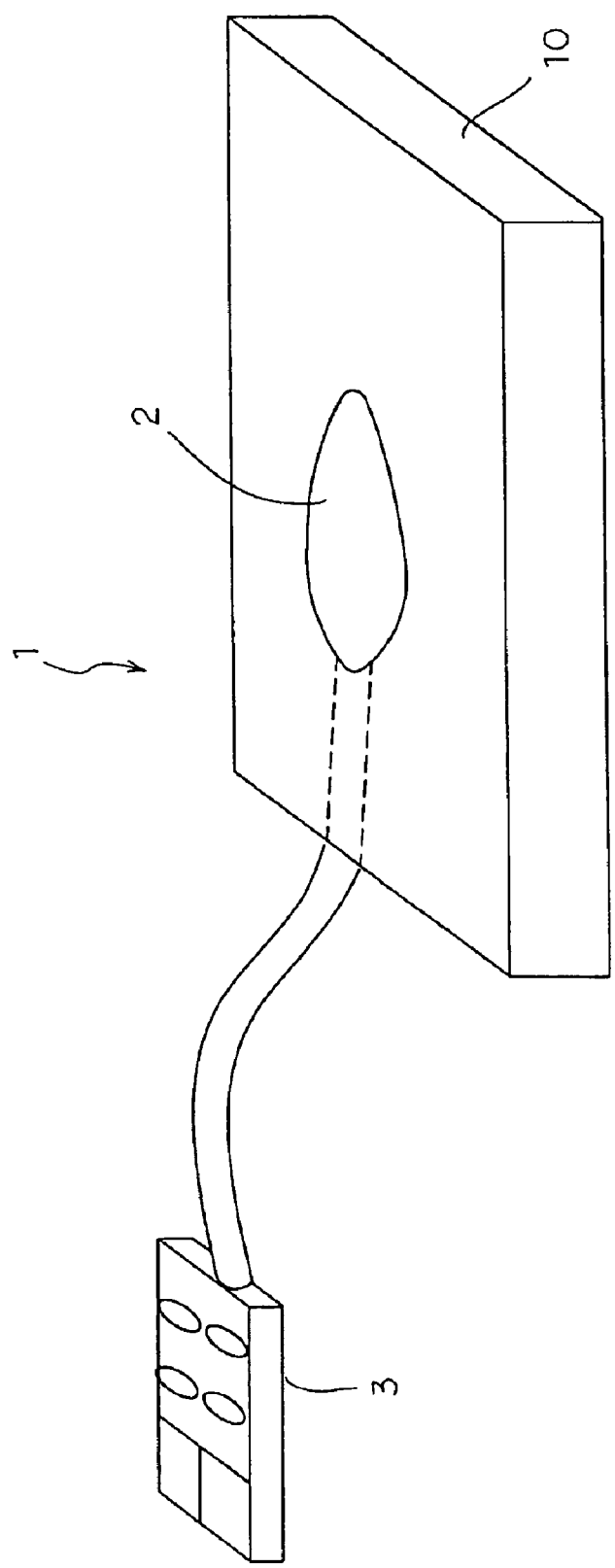
FIG. 2 is a finished product for the present invention in a preferred embodiment.

Please refer to FIG. 2 for a disclosed structure for rehabilitation equipment comprising wire fabric. The rehabilitation equipment 1 contains a rubber foam substrate 10, inside which a piece of wire containing fabric 2 uniformly is laid with one end extending out of the substrate 10 to connect to a temperature controller 3 that is composed of an installed lithium battery 30 (not indicated in the figure) and a programmable chip controller 31 (not indicated in the figure). The said rubber foam does not absorb medicine. For application, the user applies the medicine to injured area, which is then covered by the auxiliary rehabilitation equipment 1. The temperature is set on the temperature controller 3. The wire containing fabric 2 buried inside the substrate 10 continuously releases heat and maintains at a constant preset temperature. As a result, the pores of the skin in the injured area will open up to facilitate the permeation of medicine into the body. Particularly, due to far-IR emitted from the wire fabric, the injured area will warm up and be activated after application of continuous electric current, this further promotes blood circulation and metabolism in the injured area and gives rehabilitation effect.

Further, the heat released by the wire containing fabric 2 can sustain the temperature up to 75° C., much higher than ordinary wire fabric in the market. This wire containing product provides broader application range and enhanced rehabilitation effect.

Further, the said temperature controller 3 uses internal DC lithium battery 30 as power source, giving better voltage stabilization than traditional products. Besides, DC does not cause concerns over electromagnetic waves. Moreover, the temperature controller 3 automatically sustains a constant temperature once the set temperature is reached. When temperature drops, it automatically increases the temperature to the preset level. Certainly, it is power saving.

Figure 3:
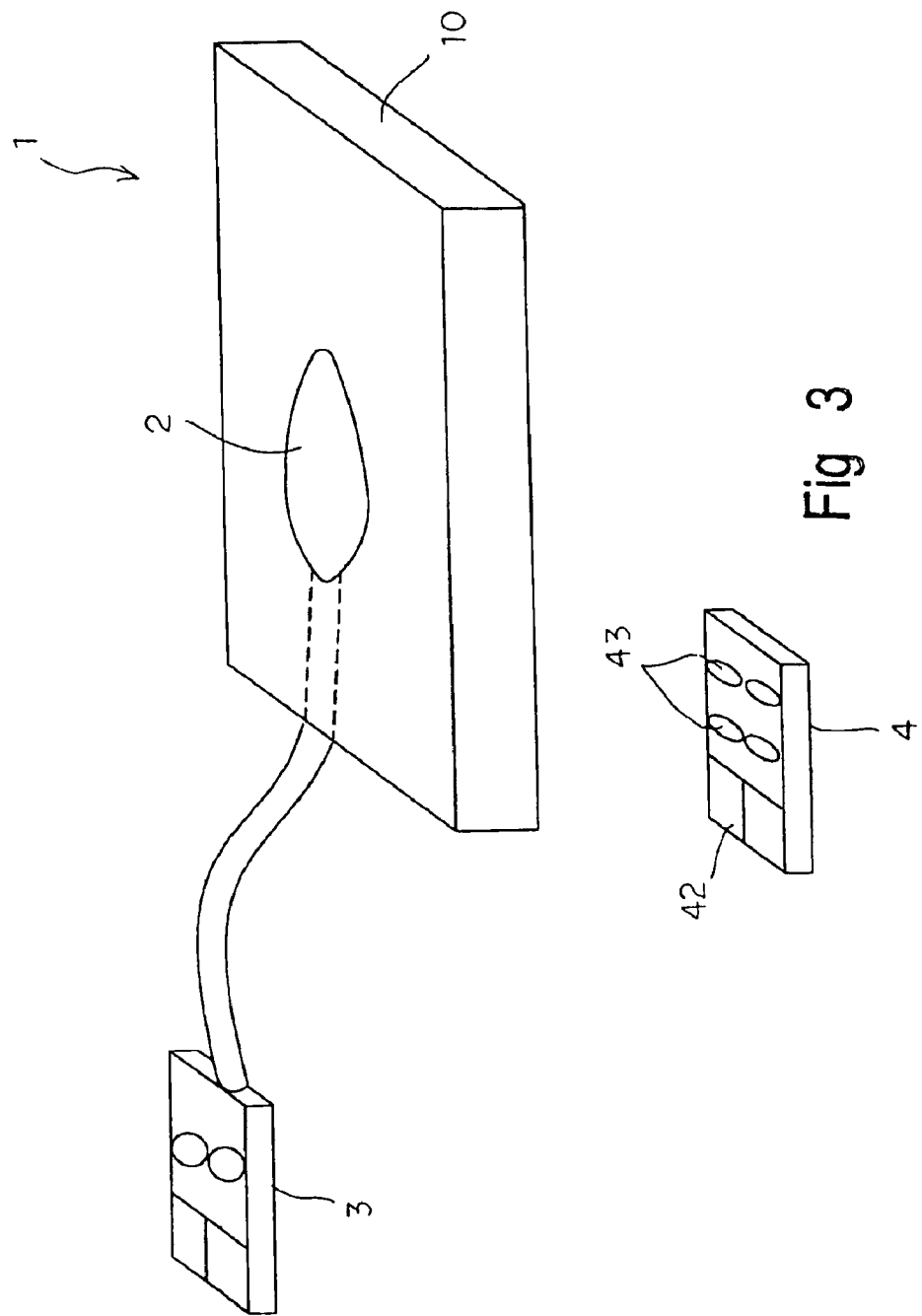
FIG. 3 is an illustration for a remote control structure in a preferred embodiment for the present invention.

Further, to remove the space restriction for the said rehabilitation equipment 1, it adds a signal-receiving unit to the programmable chip controller 31 in the temperature controller 3. With a remote control 4, the unit forms a special structure of a subunit (rehabilitation equipment) and a main unit (a remote control). The remote control 4 is shown in FIG. 3 and contains internally at least a temperature control unit 40 for the user to set a therapy temperature, a time control unit 41 for therapy time setup (not shown) and externally a liquid crystal display unit 42 to show the current settings for temperature and time, and several function buttons 43 for operation setting. Thus, the user can use the remote control to operate the rehabilitation equipment 1.

Figure 4:
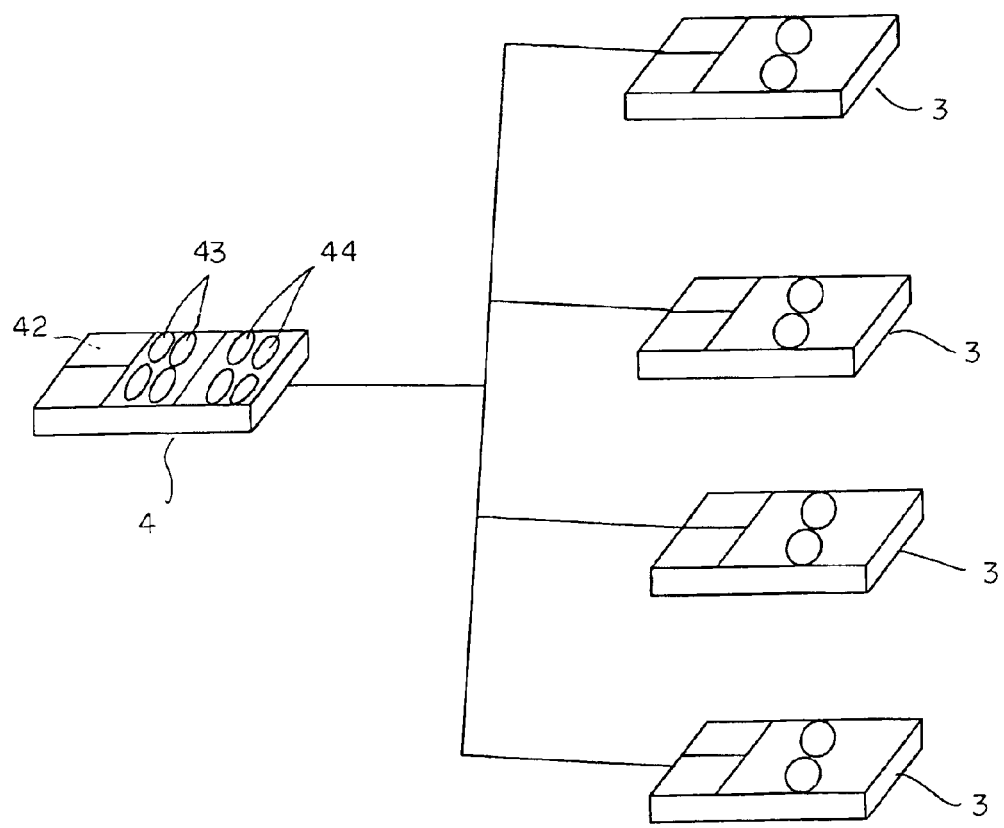
FIG. 4 is an illustration for a remote control structure in another preferred embodiment for the present invention.

The present invention can make the single unit rehabilitation equipment into a structure comprising a subunit (rehabilitation equipment) and a main unit (a remote control). Besides, the present invention can be further extended to a structure that comprises a main unit (a remote control) and multiple subunits (rehabilitation equipment). As shown in FIG. 4, the remote control 4 has several additional subunit buttons 44 for rehabilitation equipment 1. For operation, after setting the temperature for each individual subunit, the rehabilitation equipment will cover different areas for a single user or multiple users. Thus, convenience is provided for use of the product and wide range of applications can be found for the present invention.

Figure 5:
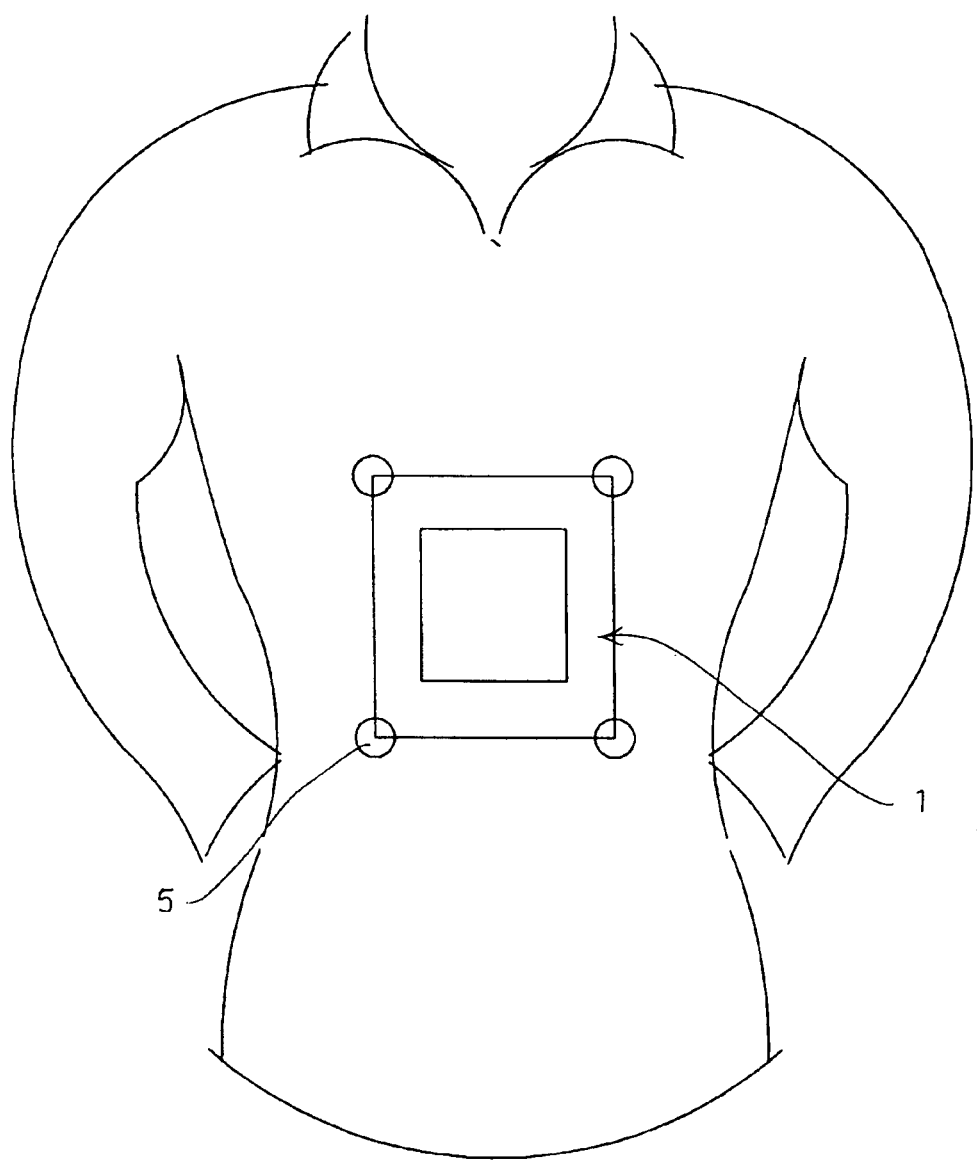
FIG. 5 an illustration for a finished product in a preferred embodiment for the present invention.

In addition, as shown in FIG. 5, it discloses insulating clothes for cold area. The said rehabilitation equipment has several joint structures 5 like female-male fasteners or Velcro around the substrate to match the similar joint structures in clothes, so the rehabilitation equipment 1 is combined with the clothes. Thus, when the user wears the clothes, the temperature controller 3 can be operated directly or by a remote control 4 to set the optimum temperature and achieve insulation effect.

Further, when the said wire containing fabric 2 is adopted for insulating clothes, the clothes is preferably flexible material with lightweight, thinness and fine touch feeling, so wearing comfort can be provided.

Further, the joint structures 5 like female-male fasteners or Velcro are preferable, because they provide firm fixation, easy disassembly and assembly, and easy cleaning.

In general, when the said wire containing fabric is used for various finished products, it will provide the following features:

1. The substrate for the rehabilitation equipment is made from rubber foam, but not ordinary cloth, so it does not absorb medicine applied on the injured area and the rehabilitation effect can be maintained.
2. Direct and remote temperature control is available. There is no restriction on space and location. Therefore, it offers great convenience.
3. DC lithium battery is used as power source. There is no concern about electromagnetic wave. Because it is recyclable, it meets environmental protection requirements.
4. Programmable chip is used for temperature control, so constant temperature can be maintained after it starts heating up. There is no risk of burning. It offers high safety level. Because it does not discharge continuously, it saves and effectively sustains power.
5. It is easy to add on clothes or removed from clothes. Washing is also allowed to give cleanness and hygiene.
6. Direct heating to a constant temperature provides quick and clear effect. The maximum temperature is up to 75° C. It offers broad range of applications and good therapy effect.
7. A remote control is used to allow a structure for a set of subunit and main unit. Or a main unit can be used with multiple subunits, so it can provide proper rehabilitation to several injured areas for a single user or multiple users.

To sum up, the heating wire containing fabric after practical evaluation proves to possess the above multiple features. Sufficiently, it is considered to be an innovation, based on which a patent application is filed.

What is claimed is:

1. An electrically conductive and heating wire containing fabric, characterized in following manufacturing steps:

A. selecting a conductive metal wire and a natural fiber;
   B. processing through yarn feeding equipment to wrap the natural fiber by the metal wire to form a metal containing yarn;
   C. weaving the metal containing yarn through a circular loom into a circular hollow shape fabric;
   D. shaping the circular hollow wire fabric by pressing into a flat shape to improve consistency in electric conductivity; and covering the wire containing fabric with natural long fiber or short staple fiber to produce the wire containing fabric.

2. The electrically conductive and heating wire containing fabric of claim 1, wherein said metal yarn has diameter between 0.035 mm and 0.08 mm.

3. The electrically conductive and heating wire containing fabric of claim 1, wherein said natural fiber is wool, rabbit fur, far-IR treated silk or elastic fiber.

4. The electrically conductive and heating wire containing fabric of claim 1, wherein optimum coil density for said metal wire wrapped around said natural fiber is 3~64 coils for 1-cm natural fiber.

5. The electrically conductive and heating wire containing fabric of claim 1, wherein said circular hollow wire has diameter between 0.1 cm and 1 cm.

6. An auxiliary rehabilitation equipment comprises a rubber foam substrate with a piece of wire fabric laid evenly inside a proper location with one end extending out of said substrate to connect to a built-in lithium battery and a temperature controller with a programmable chip controller and wherein a programmable chip controller in a temperature controller possesses temperature control function and has a signal-receiving unit with a long distance remote control so as to form a structure of a subunit (rehabilitation equipment) and a main unit (a remote control) wherein said remote control at least comprises a temperature control unit for setting up therapy temperature, a time control unit for setting up therapy time, a liquid crystal display to indicate actual temperature and therapy time, and function buttons for operation setting.

7. The auxiliary rehabilitation equipment of claim 6, or wherein said remote control can further form a configuration comprising one main unit and several subunits.

* * * * *